United States Patent [19]

Balthazor et al.

[11] Patent Number: 4,617,415
[45] Date of Patent: Oct. 14, 1986

[54] α-SUBSTITUTED N-PHOSPHONOMETHYLIMINODIACETIC ACID

[75] Inventors: Terry M. Balthazor, University City; Mitchell J. Pulwer, St. Louis, both of Mo.

[73] Assignee: Monsanto Company, St. Louis, Mo.

[21] Appl. No.: 743,213

[22] Filed: Jun. 10, 1985

Related U.S. Application Data

[62] Division of Ser. No. 557,727, Dec. 2, 1983.

[51] Int. Cl.$^4$ .............................................. C07F 9/40
[52] U.S. Cl. .................................................. 558/169
[58] Field of Search .......................... 260/942; 558/169

[56] References Cited

U.S. PATENT DOCUMENTS 3,275,677  9/1966  Allen, Jr. et al. .................... 564/157
3,969,398  7/1976  Hershman .................... 260/502.5 F

OTHER PUBLICATIONS

Wagner et al., "Synthetic Organic Chemistry", (1951) pp. 412–413 and 604–605.

Primary Examiner—Anton H. Sutto
Attorney, Agent, or Firm—Frank D. Shearin; Raymond C. Loyer

[57] ABSTRACT

A process for the preparation of a glyphosate product. An α-substituted N-phosphonomethylamino diacetic acid substrate is contacted in an aqueous medium with molecular oxygen in the presence of a catalyst for the oxidative cleavage of a substituent from the imino nitrogen of the substrate. Cleavage produces a glyphosate product, carbon dioxide, a higher aldehyde, or ketone. Novel intermediates and methods of preparation thereof are also disclosed.

2 Claims, No Drawings

α-SUBSTITUTED N-PHOSPHONOMETHYLIMINODIACETIC ACID

This is a division of application Ser. No. 557,727, filed 12/2/83.

BACKGROUND OF THE INVENTION

This invention relates to the preparation of N-phosphonomethylglycine or its derivatives and, more particularly, to an improved process for producing N-phosphonomethylglycine by oxidation of certain α-alkyl-substituted phosphonomethyliminodiacetic acid intermediates.

N-phosphonomethylglycine, known in the agricultural chemical art as glyphosate, is a highly effective and commercially important phytotoxicant useful in controlling the growth of germinating seeds, emerging seedlings, maturing and established woody and herbaceous vegetation, and aquatic plants. Glyphosate, and various inorganic and amine salts thereof, is conveniently applied in the form of an aqueous solution as a post-emergent phytotoxicant or herbicide for the selective control of one or more monocotyledonous species and one or more dicotyledonous species in the presence of other monocotyledons and dicotyledons. Moreover, such compounds are characterized by broad spectrum activity, i.e., they control the growth of a wide variety of plants, including but not limited to ferns, conifers, aquatic monocotyledons, and dicotyledons.

Hershman U.S. Pat. No. 3,969,398 describes a commercially suitable process for the manufacture of glyphosate in which iminodiacetic acid is reacted with formaldehyde and phosphorous acid to produce the intermediate N-phosphonomethyliminodiacetic acid, which is then oxidized for cleavage of one of the acetic acid substituents to produce glyphosate, release carbon dioxide and produce formaldehyde as a by-product.

Parry et al U.S. Pat. No. 3,956,370 describes a process for preparing N-phoshonomethylglycine in which N-benzylglycine is reacted with formaldehyde and phosphorous acid in an acidic aqueous medium to give N-benzyl-N-phosphonomethylglycine. Thereafter the N-benzyl group is cleaved by reaction with hydrobromic or hydroiodic acid to produce glyphosate.

Gaertner U.S. Pat. No. 3,927,080 describes the production of glyphosate by acid hydrolysis of N-t-butyl-N-phosphonomethylglycine or its esters. Tertiary butyl amine is reacted with a bromoacetate ester to produce an ester of N-t-butylglycine, which is in turn reacted with formaldehyde and phosphorous acid to produce the N-t-butyl-N-phosphonomethylglycine precursor.

SUMMARY OF THE INVENTION

It is an object of the present invention to provide a novel process for the preparation of glyphosate. It is a particular object of the invention to provide such a process in which the production of by-product formaldehyde is minimized. It is a further object of the invention to provide such a process which minimizes secondary reactions which may form unwanted by-products.

Additional objects of the invention include the provision of novel intermediates for the preparation of glyphosate and processes for the preparation of such intermediates.

Briefly, therefore, the present invention is directed to a process for the preparation of a glyphosate product corresponding to the structural formula

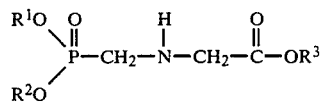

in which each of $R^1$ and $R^2$ is hydrogen, lower alkyl, aryl, or a salt-forming cation. $R^3$ is hydrogen or a salt-forming cation. The process comprises contacting an α-substituted N-phosphonomethyliminodiacetic acid substrate in an aqueous medium with molecular oxygen in the presence of a catalyst for the oxidative cleavage of a substituent from the imino nitrogen of said substrate. The substrate corresponds to the structural formula

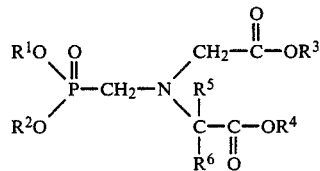

where $R^1$, $R^2$, and $R^3$ are as defined above, not more than one of $R^1$ and $R^2$ being a salt-forming cation. $R^4$ is hydrogen, lower alkyl, aryl, or a salt-forming cation. $R^5$ and $R^6$ are independently selected from among hydrogen, alkyl, aryl, substituted alkyl, and substituted aryl, not more than one of $R^5$ and $R^6$ being hydrogen. The moiety

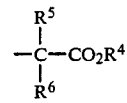

is cleaved from the imino nitrogen or said substrate, producing a glyphosate product and a carbonyl compound corresponding to the formula

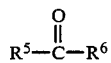

The invention is further directed to a novel compound corresponding to the structural formula

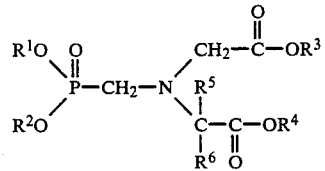

where $R^1$, $R^2$, $R^4$, and $R^3$ are hydrogen, lower alkyl, aryl, or a salt-forming cation. $R^5$ and $R^6$ are independently selected from among hydrogen, alkyl, aryl, substituted alkyl, and substituted aryl, not more than one of $R^5$ and $R^6$ being hydrogen.

Further included in the invention is a novel process for producing a compound corresponding to the structural formula

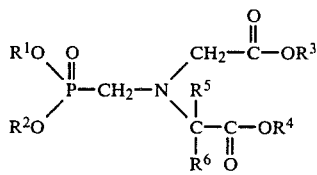

where each of $R^1$, $R^2$, $R^4$, and $R^3$ are hydrogen, lower alkyl, aryl, or a salt-forming cation. $R^5$ and $R^6$ are as defined above. The process comprising reacting an α-substituted iminodiacetic acid or ester thereof corresponding to the formula

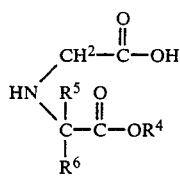

where $R^4$ is hydrogen, lower alkyl, or aryl and $R^5$ and $R^6$ are as defined above, in an acidic aqueous medium with phosphorous acid and formaldehyde.

The invention is further directed to a novel compound corresponding to the formula

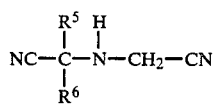

when $R^5$ and $R^6$ are as defined above.

Other objects and features will be in part apparent and in part pointed out hereinafter.

DESCRIPTION OF THE PREFERRED EMBODIMENTS

In accordance with the present invention it has been discovered that glyphosate and various glyphosate salts and esters, collectively referred to hereinafter as "glyphosate products", can be produced by oxidation of an α-substituted phosphonomethyliminodiacetic acid such as N-(carboxymethyl)-N-(phosphonomethyl)-D,L-alanine or N-(carboxymethyl)-N-(phosphonomethyl)-α-aminoisobutyric acid. Oxidative cleavage of the alanine or α-aminoisobutyric acid moiety produces the desired product while releasing carbon dioxide and producing a by-product carbonyl compound, whose structure is based on the substituted methylene group interposed between the nitrogen and the carboxyl group of the α-substituted acid carboxylic moiety.

Depending on reaction conditions, some cleavage of the unsubstituted acetic acid group may also be incurred. However, by utilizing the preferred substrate and conditions as discussed hereinbelow, the reaction predominantly yields the desired glyphosate product. In such instance, formation of by-product formaldehyde is minimized, which consequently limits the amount of N-methylated glyphosate that is formed.

Generally, the substrate utilized in the oxidative cleavage reaction of the invention corresponds to the structural formula

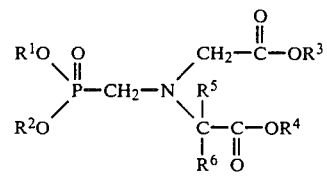

In this structure, each of $R^1$ and $R^2$ is hydrogen, lower alkyl, aryl, or a salt-forming cation. Typically, the cation may be an alkali metal, ammonium, substituted ammonium, phosphonium, substituted phosphonium, sulfonium, or substituted sulfonium. Other salts can be used, particularly those which are more soluble in water than the free acid species of the substrate. $R^3$ may be either hydrogen or a salt-forming cation of the aforesaid type. $R^4$ is hydrogen, lower alkyl, aryl, or a salt-forming cation of the aforesaid type. $R^5$ and $R^6$ are each either hydrogen, alkyl, aryl, substituted alkyl, or substituted aryl. Thus, for example, either or both of $R^5$ and $R^6$ may be methyl, ethyl, propyl, methoxymethyl, phenyl, methoxyphenyl, or the like. However, not more than one of $R^5$ and $R^6$ is hydrogen.

In accordance with the process of the invention, the substrate, and a catalyst for the oxidative cleavage of a substituent from the imino nitrogen thereof, are contacted with molecular oxygen in an aqueous medium. In order to maximize productivity of the process, the concentration of substrate in the medium is preferably as high as feasible. It has been found that feasibility of the reaction is not limited by the solubility of substrate in the medium. Thus, the reaction can be carried out in an agitated slurry in which a solid substrate is suspended in a solution that is saturated with respect to the substrate. As the cleavage reaction proceeds, solid substrate is progressively dissolved in the aqueous medium, thereby replenishing the supply of substrate and producing a final reaction mixture containing a high concentration of the glyphosate product.

Conveniently, water, the substrate, and catalyst are initially mixed and the substrate threafter reacted with oxygen by contacting the aqueous medium with a gas which contains molecular oxygen. The catalyst may be activated carbon or a transition metal, such as platinum, palladium, or rhodium on a carbon support. At a given temperature and catalyst loading, the platinum metal catalyst provides an approximately six-fold more rapid reaction than does activated carbon but, given the relative cost of the catalysts, and the complications and potential problems involved in catalyst recovery, activated carbon is considered to be equal or superior to a platinum metal on carbon as the catalyst for a commercial process.

Various activated carbons can be used by themselves or as supports for transition metal catalysts. Among the suitable carbons are those disclosed in Hershman U.S. Pat. No. 3,969,398, which is expressly incorporated herein by reference. Also suitable are the products of American Norit, sold under the designations Norit W20, F, FQA, SA4, PN3, A, ZN2, 211, CA3, and SX3; the Calgon Corporation products sold under the designations Calgon BL, RC, and C; and the ICI Americas, Inc. products sold under the designations Darco FM-1, TRS, S51, S-51FF, S-51K, BG, and KB; and the Westvaco Corporation products sold under the designations Nuchar Aqua-Pac, Aqua S, and 109. Either powdered or granular forms of carbon can be used. The proportions of granular or powdered activated carbon employed in the process of the invention generally range from between about 0.5 to about 100 or more parts by weight for every 100 parts by weight of α-substituted N-phosphonomethyliminodiacetic acid substrate employed in the process. Conveniently, the process is carried out batchwise in a stirred tank reactor, but may also be conducted in a tubular continuous reactor packed with activated carbon. In the case of a stirred tank reactor and a powdered activated carbon, it is preferred to employ from between about 1 and about 20 parts by weight of activated carbon for each 100 parts by weight of the substrate. For activated carbon in granular form, a stirred tank reaction system preferably contains between about 10 and about 75 parts by weight carbon per 100 parts by weight substrate and, more preferably, 20 parts by weight to 60 parts by weight carbon per 100 parts by weight substrate. In a continuous tubular reactor of the type mentioned above, concentrations of carbon in the reaction zone may be significantly higher than in the batch system, although the overall consumption of carbon may be approximately the same as for the batch system, or even lower.

Preferably, the oxygen containing gas comprises at least about 20% by weight oxygen and, more preferably, at least about 90% by weight oxygen. Generally, either air or pure oxygen gas may be used, although it is feasible to use other mixtures of oxygen with a gas that is inert under the conditions of the oxidative cleavage reaction. Such diluent gases may include, for example, nitrogen, argon, helium, and neon. The reaction medium is preferably contacted with oxygen at an oxygen partial pressure of between about 1 atmosphere and about 35 atmospheres absolute, more preferably between about 2.7 atmospheres and about 6.8 atmospheres gauge.

The reaction may be carried out at a temperature of between about 25° C. and about 150° C. Preferably, however, the reaction is conducted at between about 25° C. and about 75° C. where a supported transition metal catalyst is used, and at a temperature of between about 45° C. and about 110° C. where carbon alone is used as the catalyst. Oxygen consumption during the course of the reaction is normally somewhat in excess of the stoichiometric amount of one-half mole per mole of substrate. In a batch reaction system a consumption on the order of between 0.5 mole and about 1.0 mole per mole of substrate can be expected.

The oxidative cleavage reaction proceeds as follows:

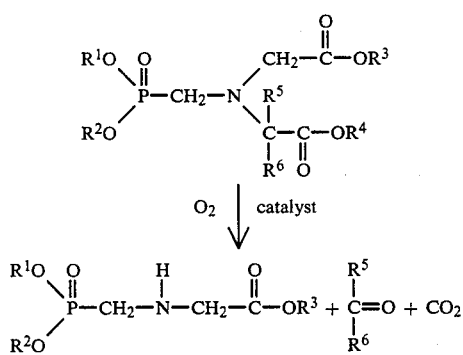

where $R^1$, $R^2$, $R^3$, $R^4$, $R^5$, and $R^6$ are all as defined above. In a preferred embodiment of the invention, the carbonyl compound can be recovered and utilized in the synthesis of additional substrate as further described hereinbelow.

Preferably, either both $R^5$ and $R^6$ are lower alkyl or one is lower alkyl and the other hydrogen. A highly suitable substrate is the α-monomethyl species N-(carboxymethyl)-N-(phosphonomethyl)-D,L-alanine. Most preferred is the α,α-dimethyl substituted compound, i.e., N-(carboxymethyl)-N-(phosphonomethyl)-α-aminoisobutyric acid. Even when the preferred substrate is used in the oxidation reaction, the unsubstituted acetic acid moiety may be cleaved to some extent, yielding a certain fraction of by-product N-phosphonomethylalanine or N-phosphonomethyl-α-aminoisobutyric acid. Although less effective than glyphosate as herbicides, these by-products can be allowed to remain in the aqueous reaction mixture as it is further processed in the conventional manner for the preparation of an aqueous herbicidal solution. It will be understood by those skilled in the art that the glyphosate product of the oxidation cleavage reaction may be modified as desired by acidification, alkalinization, esterification, or hydrolysis of ester moieties in the course of preparing a herbicidal composition. However, the preferred process comprises concentrating the solution by evaporation of a portion of the water therefrom, and/or adjustment of pH, for example to the isoelectric point.

The α-substituted N-phosphonomethyliminodiacetic acid substrates used in the process of the invention are novel compounds, as are derivatives which can be readily converted to these substrates by acidification or hydrolysis. Two processes have been discovered for the preparation of the substrate. Both involve the preparation of an α-substituted iminodiacetic acid, followed by phosphonomethylation of this acid by reaction with phosphorous acid and formaldehyde.

The the first of these methods a haloacetic acid such as chloroacetic acid is reacted in an alkaline medium with an α-substituted amino acid according to the following equation:

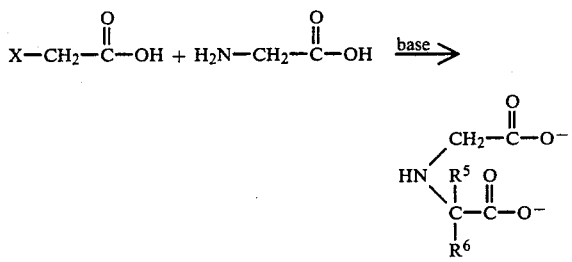

where X is halogen, and $R^5$ and $R^6$ are as defined above. Conventional bases such as sodium hydroxide, pyridine, and triethylamine may be used to scavenge the HCl produced in the condensation between the amine and halomethyl group of the haloacetic acid. Approximately stoichiometric equivalent amounts of the reactants can be utilized, and the reaction is preferably carried out at a temperature of between about 80° C. and about 150° C., conveniently at atmospheric reflux. The hydrochloride salt of the base precipitates during the course of the reaction and is separated by filtration. The product of the reaction is a salt which should be acidified, for example, by addition of hydrochloric acid, to a pH of approximately 2 or less prior to introduction into the phosphonomethylation reaction for the preparation of the novel substrate that is in turn used for the oxidative cleavage reaction described above. The acidified solution of the α-substituted iminodiacetic acid can be either subjected to evaporation under reduced pressure for recovery of the solid product, or used directly in the phosphonometylation step.

Phosphonomethylation is preferably carried out by providing an acidic aqueous medium containing the α-substituted iminodiacetic acid and a mineral acid such as hydrochloric, adding phosphorous acid to the aqueous medium, and to the resultant mixture slowly adding a solution of formaldehyde, preferably by dropwise addition. Essentially stoichiometric equivalent proportions of the α-substituted iminodiacetic acid, phosphorous acid, and formaldehyde may be used for the phosphonomethylation. Reaction is initiated at a temperature in the range of between about 80° C. and about 150° C., but the reacting mixture should be maintained at at least about 95° C. after the formaldehyde has been added. Conveniently, the reaction is carried out at atmospheric reflux over a period of approximately 1 to 5 hours. On an initial charge basis, the reaction medium preferably contains between about 5% and about 20% by weight of the α-substituted iminodiacetic acid, between about 2% and about 10% by weight phosphorous acid, and between about 1% and about 5% by weight formaldehyde. The product may be recovered by crystallization from the reaction medium. Alternatively, unreacted starting material may be removed by passing the reaction solution through a chromatography column containing an ion exchange resin and eluting the product with water. Either the eluate or the redissolved product of crystallization may be used as the aqueous medium for the oxidative cleavage reaction.

In an alternative and preferred method for preparing the α-substituted N-phosphonomethyliminodiacetic acid intermediate substrate, aminoacetonitrile is reacted with a cyanohydrin to produce an α-substituted iminodiacetonitrile.

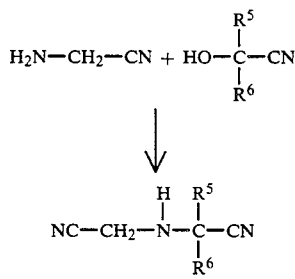

and the α-substituted diacetonitrile is hydrolyzed to produce the α-substituted iminodiacetic acid.

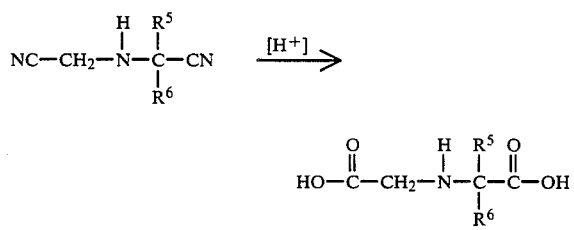

The latter in turn is converted into the α-substituted N-phosphonomethyliminodiacetic acid intermediate via the phosphonomethylation reaction as described above.

Where aminoacetonitrile is provided in the form of its hydrochloride, the reaction between it and the cyanohydrin compound is carried out in an aqueous medium in the presence of a base which neutralizes the hydrochloride. Irrespective of whether the free amino or hydrochloride salt is used, the reaction should be conducted at a pH of 7.0 or greater. The reaction is preferably conducted at approximately room temperature for a period of about 4 to about 24 hours. Approximately stoichiometrically equivalent proportions of cyanohydrin and aminoacetonitrile are charged to the reaction, typically at a concentration of between about 1 and about 15 moles per liter. As the reaction proceeds to completion an organic phase comprising the product α-substituted iminodiacetonitrile separates from the aqueous reaction medium.

Residual iminodiacetonitrile reaction product may be recovered from the aqueous phase by solvent extraction. Preferably, a chlorinated solvent such as methylene dichloride or ethylene dichloride is used for such extraction. Alternatively, diethyl ether, diisopropyl ether, chloroform, or other conventional extraction solvents may be used. Ketones are preferably not used because they react with residual amine contained in the reaction mixture, thereby tending to complicate the separation process. After extraction is complete the organic layers are combined and solvent stripped off, yielding the α-substituted iminodiacetonitrile which is ready for use in the preparation of the α-substituted iminodiacetic acid. If desired, the diacetonitrile product may be dried, for example, by contact with a desiccant such as sodium sulfate, magnesium sulfate, or calcium chloride.

To prepare the α-substituted iminodiacetic acid, the diacetonitrile is hydrolyzed in an aqueous medium. Either an alkaline or acidic medium may be used, but an acidic medium is strongly preferred since the subsequent phosphonomethylation reaction is carried out in an acidic medium. If an alkaline medium is used for the hydrolysis, the product of the hydroysis must be neutralized. The hydrolysis reaction is preferably carried out at a temperature of between about 80° C. and about 150° C., conveniently at atmospheric reflux temperature. By-product ammonium chloride precipitates and is removed from the reaction medium by filtration. If desired, the filtrate can be used directly in the phosphonomethylation reaction. Alternatively, the α-substituted iminodiacetic acid (typically as hydrochloride salt) is recovered by evaporative crystallization. Preferably the crystallization is not taken completely to dryness. As long as some moisture is allowed to remain in the residue, the evaporative crystallization can be carried out at atmospheric pressure.

Where the preferred process for preparation of the intermediates is followed, the carbonyl compound produced in the cleavage reaction can be recovered and recycled for use in preparation of the cyanohydrin:

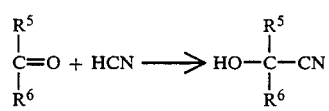

Thus, the present invention provide a unique and advantageous method for preparing glyphosate and other glyphosate products. Further, in accordance with the invention, novel and useful intermediate compounds are prepared which serve advantageously in the preparation of glyphosate and glyphosate products. Moreover, the formation of by-product formaldehyde and the N-methylation which can result from the presence of formaldehyde are minimized.

The following examples illustrate the invention.

EXAMPLE 1

Phosphorous acid (8.2 g; 0.100 mole) was added to a solution of α-methyliminodiacetic acid (14.7 g; 0.080 mole) in concentrated hydrochloric acid (50 ml), the resulting mixture stirred at a temperature, just below the reflux temperature and formaldehyde solution (3.3 g; 8.3 ml; 0.110 mole) in water (25 ml) dripped into the mixture over a 30 minute period. The resulting reaction solution was then heated at reflux for $3\frac{1}{2}$ hours after which the solvent was removed under reduced pressure leaving a yellow oil.

The oil was chromatographed by MPLC on a column containing a Dowex 50X8-400 ion exhcange resin, using water as the eluant. No separation from HCl could be seen in a 600 mm column. However, concentration of the eluate gave a solid-like residue which was recrystallized from water and ethanol to yield a white solid (16.8 g) identified as N-(phosphonomethyl)-N-(carboxymethyl)-alanine.

EXAMPLE 2

N-(phosphonomethyl)-N-(carboxymethyl)alanine produced in accordance with Example 1 (6.03 g; 0.0250 mole), activated carbon sold under the trade designation "Norit" by American Norit Company, Inc. (1.2 g), and water (100 ml) were introduced into an autoclave reactor which was thereafter sealed and heated with stirring under nitrogen to a temperature of 85° C. The nitrogen was then vented from the reactor and oxygen introduced at a pressure of 3.4 atmospheres. Reaction was carried out for 42 minutes, after which the no more starting material could be detected. Solvent was removed from the reaction mixture under reduced pressure and a precipitate formed when approximately 10 ml of the solvent remained. The precipitate was collected and recrystallized from water.

Liquid chromatography analysis of the recrystallized product showed that N-phosphonomethylglycine was present along with a sister compound whose peak on the chromatogram was of an intensity equal to that exhibited by glyphosate. The sister compound was understood to be N-phosphonomethylalanine. No N-methylglyphosate was formed, but a measurable trace of N-formylglyphosate was observed.

EXAMPLE 3

Phosphorous acid (7.32 g; 0.0893 mole) was added to a solution of α,α-dimethyliminodiacetic acid (17.6 g; 0.0893 mole) in hydrochloric acid (40 ml) and water (35 ml), and the resulting mixture stirred and heated to a temperature just below reflux. A formaldehyde solution (5.40 g; 13.5 ml; 0.18 mole) was dripped into the mixture over 3 hours and the reaction solution then heated to reflux and maintained at reflux for 15 hours. During this time, the solution turned yellow. After 15 hours at reflux the solution was cooled but no crystallization was observed. Solvent was then removed under reduced pressure and water added and evaporated under reduced pressure. Water addition and removal was repeated twice yielding a powder residue which was filtered, washed twice with cold water and then with ethanol to give a white powder that was identified as N(phosphonomethyl)-N(carboxymethyl-α-aminoisobutyric acid (17.96 g):

M.P.=204° C.–205° C. (foaming).

$^1$H NMR=(D$_2$O, NaOD, 90 MHz) δ 1.12, (s, 6H), 2.31 (d, J=11.5 Hz, 2H), 3.33 (s, 2H $^{31}$P NMR (D$_2$O, 100 MHz) δ 7.12.

IR (KBr) 3200–2900, 1731, 1710, 1536, 1486, 1465, 1428, 1381, 1328, 1275, 1249, 1217, 1178, 1083, 933, and 846 cm$^{-1}$.

EXAMPLE 4

A mixture of N-(phosphonomethyl)-N-(carboxymethyl)-α-aminoisobutyric acid produced in Example 3 (63.8 g; 0.0250 mole), Norit carbon (1.2 g) and water (100 ml) were placed in an autoclave which was sealed and heated with stirring under nitrogen to 85° C. The reactor was then vented and oxygen thereafter added at a pressure of 3.4 atm gauge. Oxygen pressure was maintained for 28 minutes until all of the starting material was consumed. Solvent was then removed under reduced pressure, leaving a white solid residue identified by NMR as containing 77% by weight glyphosate and 23% by weight N-phosphonomethyl-α,α-dimethylglycine. Liquid chromatography indicated that the product contained 93% to 98% by weight glyphosate, 8% by weight of the α,α-dimethyl analog, and traces of N-formyl substituted glyphosate.

EXAMPLE 5

Sodium carbonate (26.5 g) was added to a well-stirred solution of aminoacetonitrile hydrochloride (46.0 g; 0.50 mole) in water (200 ml) and the resulting mixture stirred for 30 minutes, after which the yellow solution obtained was treated by dropwise addition of acetone cyanohydrin (42.5 g; 45.6 ml; 0.50 mole) over a 30 minute period. The resultant mixture was stirred for 24 hours, during which time 2 layers separated. Methylene chloride was added and the mixture stirred for an additional 30 minutes, after which the 2 layers were separated and the aqueous layer extracted 3 times with methylene chloride and the extracts combined with the organic layer from the initial separation. The combined organic extract was dried over sodium sulfate, after which solvent was removed under reduced pressure, leaving an orange liquid (63.56 g) identified as α,α-dimethyliminodiacetonitrile.

$^1$H NMR: (CDCl$_3$, 90 MHz) δ 1.53 (s, 6H 2.16 (broad t, J=7.0 Hz, 1H), 3.68 (d J=7.0 Hz) 2H.

The orange liquid was then added dropwise over 30 minutes to stirred concentrated hydrochloric acid (300 ml) and the resulting reaction solution heated to reflux and maintained there for 36 hours befoe being cooled. A solid precipitate was collected and the mother liquor concentrated by evaporation to about 100 ml, effecting crystallization of further solids which were separated by filtration and combined with the initial precipitate. The combined precipitate was recrystallized from a minimal amount of water, yielding a product identified as α,α-dimethyliminodiacetic acid hydrochloride (65.9 g):

M.P.=231° C. d.

$^1$H NMR (D$_2$O, 90 MHz) δ 1.62 (s, 6H), 3.99 (s, 2H).

IR (KBr) 3200–2900, 1764, 1729, 1483, 1420, 1405, 1370, 1314, 1230, 1202, 1159, 899 and 829 cm$^{-1}$.

EXAMPLE 6

Formaldehyde solution (15.0 g; 37.5 ml; 0.50 mole) was added dropwise over a period of 2 hours to a solution of α-methyliminodiacetic acid (35.8 g; 0.250 mole), phosphorous acid (20.5 g; 0.250 mole), hydrochloric acid (125 ml) and water (100 ml). The reaction solution was then heated to reflux for 18 hours and cooled. Solvent was removed under reduced pressure. No crystallization was observed when the residue was treated with either hot water, ethanol, or ethanol/water mixtures with subsequent evaporation of water/ethanol. The oil product was thereafter chromatographed and the fraction continaing the desired product N-(phosphonomethyl)-N-(carboxymethyl)-alanine chromatographed 3 additional times to give an oil fraction from which a crystalline product could be recovered by dissolution in ethanol and evaporation of the solvent. The crystalline product recovered (47.6 g) showed a melting point of 190° C. and was identified as N-(phosphonomethyl)-N-(carboxymethyl)-alanine:

$^1$H NMR (D$_2$O, NaOD, DSS, 90 MHz), δ 1.46 (d J=7.5 MHz, 3H), 3.05 (d, J=11.0 Hz, 2H), 3.64 (d, J=16.0 Hz, 1H), 3.98 (dd, J=16.0 Hz and 1.5 Hz, 1H), 4.25 (q, J=7.5 Hz, 1H)

$^{31}$P NMR (D$_2$O, 100 MHz), δ 6.88.

IR (KBr) 3200–2900, 1718, 1683, 1484, 1434, 1346, 1270, 1226, 1115, 939, 883, and 845 cm$^{-1}$.

A second fraction obtained from chromatography contained a foam.

Elemental analysis of the crystalline product showed 30.00% by weight carbon, 5.06% by weight hydrogen, and 5.78% by weight nitrogen, which compared favorably with the theoretical proportions of 29.89% by weight carbon, 5.02% by weight hydrogen, and 5.81% by weight nitrogen as calculated for C$_6$H$_{12}$NO$_7$P.

EXAMPLE 7

50% by weight sodium hydroxide solution (80.0 g; 1.00 mole) was added to a solution of D,L-alanine (89.0 g; 1.00 mole) in water (100 ml) with stirring. To this solution, a solution of chloroacetic acid (95.0 g; 1.00 mole) in water (50 ml) and a further portion of 50% sodium hydroxide solution (160.0 g; 2.00 moles) were added simultaneously dropwise over a 2-hour period. The reaction solution was then stirred for 48 hours at reflux, cooled, and neutralized to pH 2 with concentrated hydrochloric acid. Solvent was removed at reduced pressure and the residue treated with boiling concentrated hydrochloric acid. The solid was recovered by filtration and the mother liquor removed under reduced pressure, yielding a white solid which was recrystallized from water. The recrystallized product (104.5 g) had a melting point of 218° C. to 220° C. (water:acetic acid), and analyzed for elemental content, was found to contain 32.73% by weight carbon, 5.00% by weight hydrogen, 19.37% by weight chlorine, and 7.63% by weight nitrogen, which compared favorably with the theoretical proportions of 32.71% by weight carbon, 5.49% by weight hydrogen, 19.31% by weight chlorine, and 7.63% by weight nitrogen calculated for C$_5$H$_{10}$ClNO$_4$. The product was further identified as α-methyliminodiacetic acid as follows:

$^1$H NMR (D$_2$O, DSS, 90 MHz) δ 1.64 (d J=7.5 Hz, 3H), 4.08 (s, 2H), 4.22 (q, J=7.5 Hz, 1H).

IR (KBr) 3200–2900, 1765, 1736, 1553, 1476, 1413, 1377, 1279, 1202, 1135, 1112, 1079, 1052, 1001, 919, 859 cm$^{-1}$.

EXAMPLE 8

The glyphosate intermediate prepared in Example 3 (6.38 g), 10% platinum on carbon catalyst (1.2 g) and water (100 ml) were added to an autoclave which was sealed with nitrogen and heated with stirring to 85° C. Thereafter, the reactor was vented and oxygen added to a pressure of 3.4 atmospheres. The reaction was observed to be complete within seven minutes.

Liquid chromatography analysis showed that the ratio of glyphosate to its α,α-dimethyl analog was approximately the same as when carbon alone was used as the catalyst.

EXAMPLE 9

N-(phosphonomethyl)-N-(methylcarboxymethyl)-α,α-aminoisobutyric acid (6.38 g; 0.025 mole), water (100 ml), and 10% platinum on carbon catalyst (1.2 g) were added to an autoclave reactor, and the reactor was sealed and heated to 45° C. under nitrogen. Thereafter, the reactor was vented and oxygen added to a pressure of 3.4 atm, after which the reaction was carried out for 2 hours while monitoring its progress by NMR.

After 2 hours, the oxygen was vented, nitrogen added and vented 10 times, and the reaction mixture then heated to 85° C. to dissolve all material contained therein so that it could be removed from the reactor. An HPLC scan of the reaction mixture showed almost the exact same ratio of glyphosate as its α,α-dimethyl analog as when the oxidation was run at 85° C.

In view of the above, it will be seen that the several objects of the invention are achieved and other advantageous results attained.

As various changes could be made in the above methods and products without departing from the scope of the invention, it is intended that all matter contained in the above description or shown in the accompanying drawings shall be interpreted as illustrative and not in a limiting sense.

What is claimed is:

1. A compound corresponding to the formula

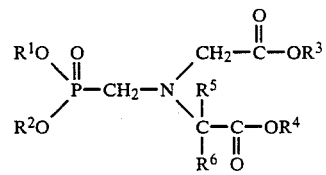

where R$^1$, R$^2$, R$^3$, and R$^4$ are independently selected from the group consisting of hydrogen, lower alkyl, aryl, and a salt-forming cation, and R$^5$ and R$^6$ are independently selected from the group consisting of hydrogen, alkyl, aryl, substituted alkyl, and substituted aryl, not more than one of R$^5$ and R$^6$ being hydrogen.

2. A compound as set forth in claim 1 wherein both R$^5$ and R$^6$ are methyl.

* * * * *